United States Patent [19]

Sogawa et al.

[11] Patent Number: 4,969,709
[45] Date of Patent: Nov. 13, 1990

[54] MECHANISM FOR BENDING ELONGATED BODY

[75] Inventors: Ichiro Sogawa; Nao-omi Maeda; Kazuhiko Hayashi; Masahiko Kanda; Koro Yotsuya, all of Osaka, Japan

[73] Assignee: Sumitomo Electric Industries, Ltd., Osaka, Japan

[21] Appl. No.: 420,498

[22] Filed: Oct. 11, 1989

Related U.S. Application Data

[63] Continuation of Ser. No. 153,910, Feb. 9, 1988, Pat. No. 4,904,048.

[30] Foreign Application Priority Data

| Feb. 9, 1987 | [JP] | Japan | 62-28640 |
| Feb. 9, 1987 | [JP] | Japan | 62-28641 |
| Feb. 9, 1987 | [JP] | Japan | 62-28642 |
| Feb. 9, 1987 | [JP] | Japan | 62-28643 |
| Feb. 9, 1987 | [JP] | Japan | 62-28644 |

[51] Int. Cl.$^5$ .................................. G02B 23/26
[52] U.S. Cl. ......................... 350/96.26; 350/96.29; 350/96.3; 128/4
[58] Field of Search ............... 350/96.2, 96.26, 96.23, 350/96.29, 96.3; 128/1-8

[56] References Cited

U.S. PATENT DOCUMENTS

| 4,601,283 | 7/1986 | Chikama ..................... 128/4 |
| 4,742,817 | 5/1988 | Kawashima et al. ......... 128/4 |
| 4,753,223 | 6/1988 | Bremer ........................ 128/4 |
| 4,790,624 | 4/1988 | Van Hoye et al. ......... 350/96.26 |
| 4,904,048 | 2/1990 | Sogawa et al. ............. 350/96.26 |

FOREIGN PATENT DOCUMENTS 0208175  1/1987  European Pat. Off. .

Primary Examiner—John D. Lee
Assistant Examiner—John Ngo
Attorney, Agent, or Firm—Sughrue, Mion, Zinn, Macpeak & Seas

[57] ABSTRACT

A mechanism for bending an elongated body such as the tube of an endoscope without the use of electric elements, thereby eliminating a shock hazard. A shape-memorizing alloy is inserted into the elongated body at portions to be bent. In some embodiments, heat for causing the shape-memorizing alloy and hence the elongated body to bend is produced by light carried by an optical fiber, while in other embodiments frictional heat produced by a mechanism vibrator is employed. In some embodiments using light, a shutter arrangement is added to control the heating of the shape-memorizing alloy.

9 Claims, 9 Drawing Sheets

//4,969,709

MECHANISM FOR BENDING ELONGATED BODY

This is a continuation of application No. 07/153,910 filed Feb. 9, 1988 which has been allowed (Pat. No. 4,904,048).

BACKGROUND OF THE INVENTION

The present invention relates to a mechanism for bending an elongated body, and more particularly, to a mechanism for bending an elongated body suitable for use in an endoscope or the like.

A wide variety of endoscopes have heretofore been available, all of which include bendable elongated body portions, for observing the interior of various organs such as blood vessel, coelomata, and the like. Various mechanisms for bending such an elongated body will be considered.

As illustrated in FIG. 1, one well-known mechanism, as disclosed in Japanese Utility Model Publication No. 13033/1974, includes a bending tube 62 composed of a multiplicity of nodal rings 61, the central portions of which are formed with fulcrum portions 60 and encasing a segment of fiber 63, and a several of wires 64, first ends of which are fixed to a nodal ring 61 disposed at the tip portion thereof, the wires 64 being inserted through other nodal rings 61. Another well-known bending mechanism, as disclosed in Japanese Laid-Open Patent Publication No. 25140/1983, is composed of a multiplicity of articulated pieces, shape-memorizing alloys provided between the articulated pieces, and a heating device for bending the shape-memorizing alloys in predetermined shapes by heating them with a supplied electric current.

The above-described mechanisms for bending an elongated body function by manipulating the wires and heating the shape-memorizing alloys by the heating device, thereby bending the multiplicity of nodal rings or articulated pieces. The tip portion of the elongated body can be bent at a predetermined angle, which permits observation of desired portions within a vascular tract or the like.

Because, however, the former type of mechanism for bending the elongated body includes a multiplicity of nodal rings and wires required for the bending operation, the structure is complicated. It is therefore difficult to reduce the diameter of the elongated body, resulting in a limitation in the observable diameter of the organ or the like. Consequently, there arises a problem in that ulcers, tumors or the like cannot be detected in their early stages. The amount of bending of the elongated body is adjusted in accordance with the degree to which the wires are moved when observing various organs. Hence, this adjustment leads to problems wherein the operation of bending the elongated body becomes intricate and it is difficult to bend the body at a desired angle with high accuracy.

The latter type of bending mechanism is accompanied by problems in addition to those inherent in the former bending mechanism because of the provision of the multiplicity of articulated pieces. To be specific, since the device for heating the shape-memorizing alloy employs an electrically energized heating system, when the elongated body is employed as an endoscope, there may be a danger of electric shock. The practical applications of such an arrangement are restricted.

SUMMARY OF THE INVENTION

It is a primary object of the present invention, which has been made in light of the above-described problems, to provide a mechanism for bending an elongated body having a simplified structure, which results in a reduced diameter of the elongated body, and with which the elongated body can be accurately bent at a desired angle by a simple operation, and which is also usable for a wide range of applications with no possibility of causing an electric shock.

To accomplish the above and other objects, in accordance with the invention, there is provided an improved mechanism for bending an elongated body including a segment of optical fiber, wherein the heating device comprises an optical fiber having a core for leading light used for heating and a cladding, a predetermined portion of the cladding is cut away, and a shape-memorizing alloy is provided in a position so as to be heated by light leaking from the core.

In the above-described mechanism for bending an elongated body, the cladding of the optical fiber is partially cut away and the shape-memorizing alloy is provided in this cut-away portion. The light used for heating travels through the optical fiber and leaks from the cut-away portion. The shape-memorizing alloy is heated with the leaked light beam, thereby bending the alloy in a previously memorized configuration. The shape-memorizing alloy which has been bent in the previously memorized configuration decreases in shape-holding force as it cools. However, the already-bent shape-memorizing alloy is capable of reverting to its initial form due to the resilient restoring force of the elongated body and the optical fiber.

The mechanism for bending the elongated body according to the present invention utilizes light for heating the shape-memorizing alloy, thereby eliminating the possibility of causing an electric shock. Safe operation is thus attained.

To further accomplish the above-described objects, in a further mechanism for bending an elongated body including an optical fiber, the improved mechanism according to the present invention is arranged such that the optical fiber is composed of a core for leading the light serving for heating and a cladding, a predetermined portion of the cladding is cut away, a shape-memorizing alloy is provided in the elongated body positioned adjacent the cut-away portion of the cladding, and the optical fiber is inserted into a tube for controlling the condition under which the shape-memorizing alloy is irradiated with light leaking from the cut-away portion of the cladding on the basis of a back-and-forth movement or rotation.

In thus-constructed mechanism for bending an elongated body, the predetermined portion of the cladding of the optical fiber for leading the light for heating and the shape-memorizing alloy is disposed to face to the cut-away portion of the cladding. This optical fiber is inserted into the tube, which is capable of back-and-forth movement or rotation, for controlling the irradiation of the light leaking for the cut-away portion of the optical fiber with respect to the shape-memorizing alloy. The light travels through the optical fiber and leaks from the cut-away portion, irradiating the shape-memorizing alloy and heating the same. The shape-memorizing alloy is thus bent in a previously memorized configuration.

When the light lead though the optical fiber is shielded due to the positioning movement of the tube, the heating process of the shape-memorizing alloy ceases and the alloy cools.

In further fulfillment of the above and other objects, in a mechanism for bending an elongated body including an optical fiber, an improved mechanism for bending an elongated body according to a further aspect of the present invention is arranged such that the optical fiber comprises a core for leading light serving for heating and a cladding, a predetermined portion of the cladding of the optical fiber is cut away, a shape-memorizing alloy is disposed in the cut-away portion, and a member constituting a bending part of the elongated body in which the shape-memorizing alloy is disposed has an elastic modulus which varies in the longitudinal direction thereof.

In above-described embodiment of the inventive mechanism for bending an elongated body, the bending of the shape-memorizing alloy can be controlled by adjusting the elastic modulus and the heating temperature. More specifically, where the tip of the bending part is formed of a material having a small elastic modulus, and when the light passed through the optical fiber is of a low intensity, even if the shape-memorizing alloy is heated over a transformation temperature, only the tip of the elongated body having the small elastic modulus can be bent because the heating temperature is low. On the other hand, if the heating temperature is increased by light having a high intensity, the restoring stress of the shape-memorizing alloy is augmented. As a result, the shape-memorizing alloy can be entirely bent. The shape-memorizing alloy which has been bent in the predetermined configuration decreases in shape-holding force when it cools. The already-bent shape-memorizing alloy can therefore revert to its initial shape due to the elastic restoring force of the lengthy body by adjusting the elastic modulus of the elongated body and the optical fiber. Unlike the prior art mechanism, no wire manipulating operation is required, and it is possible to reversibly bend and restore the elongated body in predetermined shapes simply by changing the intensity of light. Nodal rings and wires, which are indispensable for the prior art mechanism, are unnecessary, so that the structure is simplified and the diameter of the lengthy body can be reduced.

A mechanism for bending an elongated body according to a still further aspect of the present invention is characterized by a shape-memorizing alloy disposed in such a portion within an elongated body corresponding to a tip of an optical fiber. In this mechanism for bending the elongated body, preferably one of the optical fiber and the shape-memorizing alloy is inserted into the elongated body in such a manner as to be capable of undergoing a back-and-forth movement therein. It is also desirable that the tip portion of the cladding of the optical fiber be cut away.

The thus-constructed mechanism for bending an elongated body takes advantage of the fact that the tip of the optical fiber remarkably increases in temperature when light travels through the optical fiber. Namely the shape-memorizing alloy is disposed in a portion corresponding to the tip of the optical fiber, and immediately when the light is led through the optical fiber, the tip of the optical fiber reaches a high temperature. The shape-memorizing alloy is thus heated by the optical fiber tip having a high temperature, bending the alloy in a predetermined configuration.

Where either the optical fiber or the shape-memorizing alloy is movably provided in the elongated body as described above, the heated portion of the shape-memorizing alloy is controlled by adjusting the degree to which the optical fiber and/or the shape-memorizing alloy is moved in the longitudinal direction. Thus, the shape-memorizing alloy and the elongated body can be bent in desired configurations. Where the cladding at the tip of the optical fiber is cut away, it is possible to heat the shape-memorizing alloy in a highly efficient manner.

Further in accordance with the above and other objects, a mechanism for bending an elongated body is provided comprising an exciter, a vibrating member connected to the exciter and slidably contactually disposed in a predetermined portion within the elongated body, and a shape-memorizing alloy disposed in a portion of the elongated body which corresponds to a slide-contacting portion of the vibrating member.

In the thus-constructed mechanism for bending an elongated body, the vibrating member is slidably contactually disposed in the predetermined portion within the elongated body. Consequently, when the vibrating member is vibrated by the exciter, the slide-contacting portion increases in temperature due to friction generated between the vibrating member and the elongated body. The heating temperature caused by friction can be controlled by adjusting the exciting intensity of the exciter. The shape-memorizing alloy is disposed in such a portion of the elongated body as to correspond to the slide-contacting portion of the vibrating member so that the shape-memorizing alloy is heated with the frictional heat there generated, thereby bending it in a previously memorized configuration.

DESCRIPTION OF THE PREFERRED EMBODIMENTS

Preferred embodiments of the present invention will hereinafter be described in detail with reference to the accompanying drawings.

Figure 1:
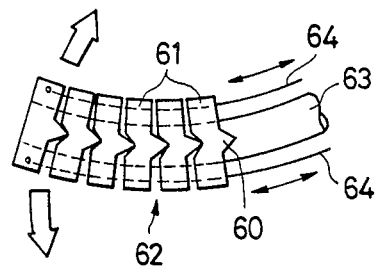
FIG. 1 is a schematic diagram showing a conventional mechanism for bending an elongated body.
Figure 2:
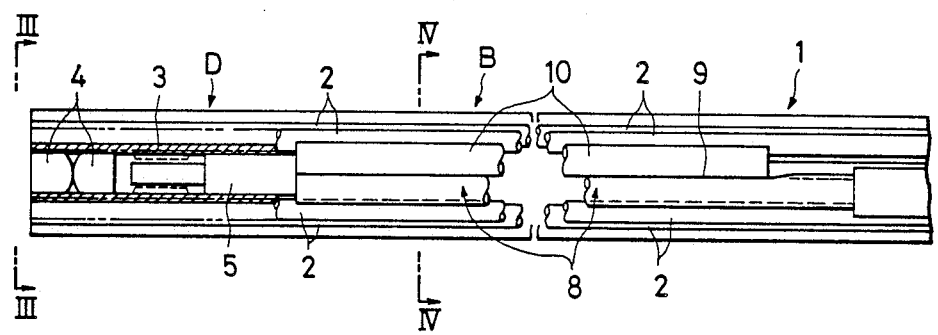
FIG. 2 is a schematic enlarged sectional view of the principal portion of a fiberscope which utilizes a mechanism for bending an elongated body constructed in accordance with a preferred embodiment of the present invention.
Figure 3:
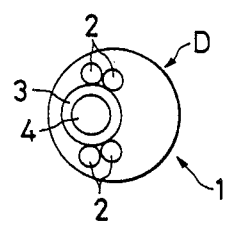
FIG. 3 is an end elevation taken substantially along a line III—III in FIG. 2.
Figure 4:
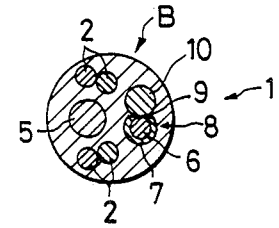
FIG. 4 is a sectional view taken substantially along a line IV—IV in FIG. 2.
Figure 5:
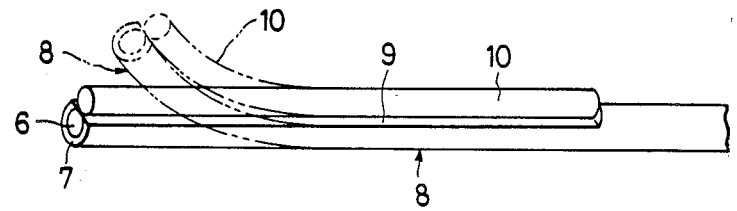
FIG. 5 is a conceptual diagram of a principal portion of the elongated body depicted in FIG. 2 illustrating an operational condition thereof.

Referring now to FIG. 2, there is illustrated schematically an enlarged sectional view of a principal portion of a fiberscope which employs a mechanism for bending an elongated body constructed according to a first preferred embodiment of the present invention. FIG. 3 is an end elevation taken substantially along a line III—III in FIG. 2. FIG. 4 is a sectional view taken substantially along a line IV—IV in FIG. 2. FIG. 5 is a conceptual diagram of a principal portion illustrating an operational condition of the elongated body shown in FIG. 2.

An elongated body 1 is constituted by a detection part D formed at the tip of the body 1 and a bending part B, including a bending mechanism provided in continuation from the detection part D. Embedded in the body 1 are light guides 2 for illuminating a portion to be detected, a lens sleeve 3 including object microlenses 4 disposed at the tip thereof, and a segment of image fiber 5, provided in continuation from the object microlenses 4, for leading the light emerging from the light guides 2 to the body portion to be observed. These components are combined to constitute the foregoing detection part D.

The bending part B disposed adjacent the embedded components of the detection part D is composed of a core 6 and a cladding 7 having a refractive index smaller than that of the core 6. This bending part B incorporates a segment of optical fiber 8 for leading laser beams serving for heating purposes.

In the cladding 7 of the optical fiber 8, a predetermined portion continuous to the detection part D is cut to a predetermined length, with the result that a portion of the beam of light leaks from the predetermined portion of the optical fiber 8. A linear shape-memorizing alloy 10 having a predetermined transformation temperature is disposed along the cut portion 9 to bend the body 1 in a predetermined configuration when the alloy 10 is heated to predetermined temperature. When an input laser beam is applied to optical fiber 8, a portion of the laser beam leaks from the cut portion 9 to heat the shape-memorizing alloy 10. As a result, the shape-memorizing alloy 10 is, as depicted by a broken line in FIG. 5, bent in the predetermined shape.

It should be noted that the core 6 and the cladding 7 of the optical fiber 8 may be formed of a variety of materials capable of leading the heating light. These materials include, e.g., quartz, glass containing multiple components, polymethyl methacrylate, silicone resin, IR fibers, and the like. It is desirable that the elongated body 1 in which the optical fiber 8 and other components are embedded be formed of synthetic resin having a flexibility similar to that of silicone resin.

The transformation temperature of the shape-memorizing alloy 10 may be set to a desired value depending upon the application. The shape-memorizing alloy 10 may be made to previously memorize a desired angle and a desired bending shape. Where the fiberscope is used as an endoscope, the transformation temperature of the shape-memorizing alloy 10 is preferably set to, for instance, 38° C. to 45° C., which is slightly higher than typical in vivo temperatures. The shape memorizing alloy 10 is not confined to linear alloys and may be diversified both in size and in configuration. The shape-memorizing alloy 10 may be any of a wide variety of known material such as a NiTi alloy containing 50 to 60% Ni by weight and 40 to 50% Ti by weight, a NiTi-series alloy, a NiAl alloy, a CuAlNi alloy, a CuSn alloy and a CuZn alloy in which Ni or Ti is partially replaced with elements such as Al, Cu, V, Zr, Cr, Mo, Fe and Co.

It is desirable that the elongated body 1 have an elastic modulus sufficient to restore the bent shape-memorizing alloy 10 to its initial form as it cools. Let the shape-holding forces of the shape-memorizing alloy 10 when undergoing the heating transformation and the cooling process be $F_1$ and $F_2$, respectively, and let the elastic restoring force of the optical fiber 8 and the elongated body 1 be f. The components except the shape-memorizing alloy 10 are preferably formed of such materials as to generally satisfy:

$$F_2 < f < F_1$$

In the thus-constructed bending mechanism, the predetermined portion of the cladding 7 of the optical fiber 8 is cut away and the shape-memorizing alloy 10 is provided in the cut portion 9. The laser beams travelling through the optical fiber leak from the cut portion 9 to heat the shape-memorizing alloy 10. Hence, no troublesome wire-manipulating operation is necessary, unlike the prior art mechanism. The shape-memorizing alloy 10 and the elongated body 1 can be bent in desired configurations in accordance with the previously memorized shape of the shape-memorizing alloy 10, thereby facilitating the observation of a given portion within a vascular tract to the like. Unlike the conventional bending mechanism, there is no necessity to provide a multiplicity of nodal rings or wires, resulting in a simplified structure and in a reduction in the diameter of the elongated body. More specifically, although employing components having a large number of functions such as the light guides 2, the image fiber 5, etc., it is possible to attain for the elongated body an extremely small outside diameter of 2.0 mm or less. It is therefore feasible to precisely observe the interior of thin vascular tracts or the coelom.

Since the device for heating the shape-memorizing alloy 10 involves only the use of the laser beams, there is no possibility of causing electric shock. Such heating can safely be applied to various organs. Hence, the application of the invention can be diversified.

The cladding 7 of the optical fiber 8 may be cut away in a desired portion in which the elongated body is to be bent. The portions of the cladding 7 which correspond to the bending portions may be entirely removed. It is desirable that the cut portion be formed at the tip of the optical fiber 8 in order to facilitate the detection of the objective portion by bending the elongated body 1. Cutting of the cladding 7 may be accomplished with a variety of known techniques, for example, mechanically, such as by grinding, or chemically, such as by etching employing various chemicals.

For the purpose of preventing axial emission of laser beams from the tip of the optical fiber 8 and to efficiently heat the shape-memorizing alloy 10, the tip end surface of the optical fiber 8 is desirably provided with a reflecting member such as a mirror and prism, or alternatively the tip end surface is coated with a reflecting film.

If the cut portion 9 of the cladding 7 is formed with a substance having a refractive index different from that of the cladding 7, as in the previous case, the shape-memorizing alloy 10 can efficiently be heated. Namely, where a substance having a refractive index different from that of the cladding 7 is employed in the above-mentioned manner, the structure of the optical fiber 8 at the cut portion 9 is more disturbed and it follows that the laser beams travelling through the optical fiber 8 more efficiently leak from the cut portion 9. Therefore, the shape-memorizing alloy 10 can be heated with high efficiency.

It is preferable that plural segments of shape-memorizing alloy 10 be fixed in a plurality of positions at given spacings to the optical fiber 8, or alternatively fixed by flexible thread-like fixing members so that the elongated body 1 is bent subsequent to the bending of the shape-memorizing alloy 10.

Following the cooling of the shape-memorizing alloy 10, the elongated body 1 quickly reverts to its initial configuration. For this purpose, the restoring force and the elastic modulus of the elongated body 1 or the optical fiber may be adjusted by coating the body 1 or the optical fiber 8 with, e.g., synthetic resin or the like.

Figure 6:
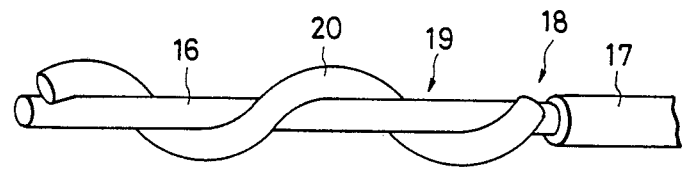
FIG. 6 is a schematic diagram illustrating another embodiment of the present invention.

The shape-memorizing alloy 10 can be provided in the cut portion of the cladding in various modes. For instance, as illustrated in FIG. 6, when using an optical fiber in which the cladding 17 positioned at the tip of the optical fiber 18 is completely cut away, the shape-memorizing alloy 20 may spirally be wound on the core 16 exposed from the cut portion 19 of the optical fiber 18.

In the above-described embodiment, the elongated body 1 is arranged to be bent in one direction by making use of the shape-memorizing alloy 10. However, a plurality of optical fibers 8 can be embedded in the elongated body 1, and plural shape-memorizing alloys 10 provided, each disposed in the cut portions 9 of respective optical fibers 8, whereby the body 1 can be bent in the multiple directions. If four segments of optical fibers 8 are used, for instance, one pair of optical fibers 8 can be arranged orthogonally to another pair of optical fibers 8. In this state, the optical fibers 8 are embedded in the elongated body 1, and the shape-memorizing alloys 10 set in the cut portions 9. The laser beams are selectively passed through the four segments of optical fibers 8, and the elongated body 1 can thereby be selectively bent in four directions.

Also, the elongated body can be bent at a plurality of positions along its length using a similar arrangement. For example, where a plurality of optical fibers 8 are used, the cut-away portions 9 are formed at different positions in the longitudinal direction. Shape-memorizing alloys 10 are provided in the respective cut-away portions 9, or alternatively shape-memorizing alloys 10 each having a different transformation temperature may be set in the several of cut-away portions 9 at the different positions in the longitudinal direction. In the former case, the bending portions of the shape-memorizing alloys 10 can be selected by permitting the transmission of the laser beams through the proper optical fibers 8 among the total optical fibers 8. Futhermore, it is possible to bend the elongated body 1 in desired configurations while varying the angle and a bending degree of each individual segment of shape-memorizing alloy 10 in several positions by simultaneously or differently leading the laser beams to the several of optical fibers 8. In the latter case the elongated body 1 can be bent in the desired shape while sequentially changing the angle and the bending degree of the shape-memorizing alloy 10 in the several of positions by sequentially applying laser beams to the optical fibers 8.

Figure 7A:
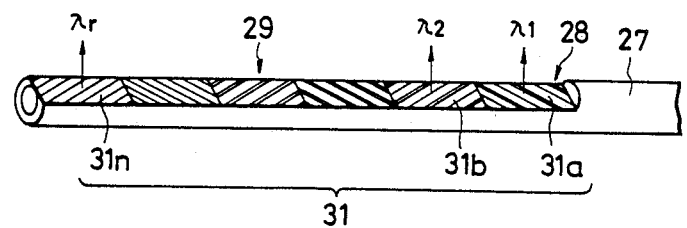
FIG. 7A is a schematic diagram of the principal portion of still another embodiment of the present invention.
Figure 7B:
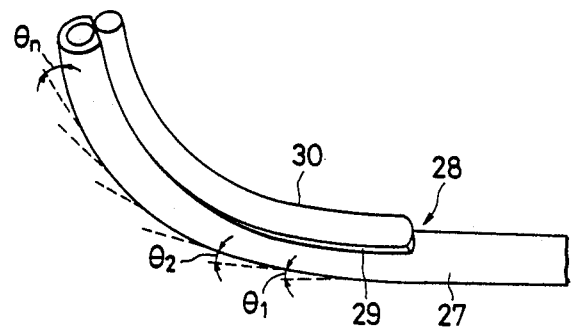
FIG. 7B is a diagram illustrating a bending condition of a shape-memorizing alloy in the embodiment of FIG. 7A.

Thin films 31 having respective absorption wavelength characteristics are, as illustrated in FIGS. 7A and 7B, sequentially formed on the cut-away portions 29 of the cladding 27 in the longitudinal direction of the optical fiber 28, and, preferably, the shape-memorizing alloy 30 is disposed on the thin film 31. In the above-described bending mechanism, for example, when using laser beams having a wavelength $\lambda_1$, such laser beams are absorbed by a thin film section (31a) of the thin film 31 which section is associated with the wavelength $\lambda_1$. As a result, a desired portion of the shape-memorizing alloy 30 can be heated. Hence, laser beams having wavelengths $\lambda_1, \lambda_2 \ldots \lambda_n$ are simultaneously absorbed at the plurality of positions corresponding to the plurality of thin film sections $31a, 31b \ldots 31n$, and at the same time the shape-memorizing alloys 30 are heated at the plurality of positions. Subsequently, the shape-memorizing alloys 30 and the elongated body 1 are sequentially bent at angles of $\theta_1, \theta_2, \ldots, \theta_n$.

If a plurality of thin films 31, each having a different absorption wavelength characteristic, are formed on the surface of the shape-memorizing alloy 30, the same effects as those described above will be exhibited. The thin films 31 each having the different absorption wavelength characteristics may be diversified in type according to the desired wavelengths of the laser beams.

Figure 8:
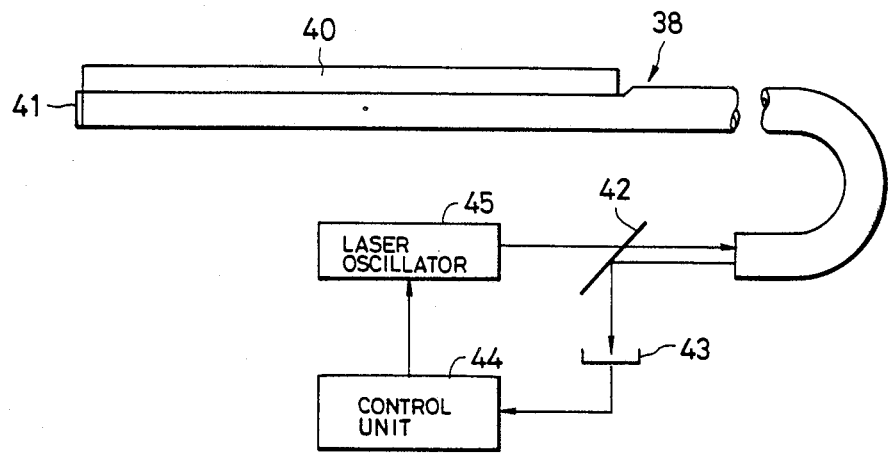
FIGS. 8 and 9 are schematic diagrams each showing an example of a control unit which uses the inventive mechanism for bending an elongated body.
Figure 9:
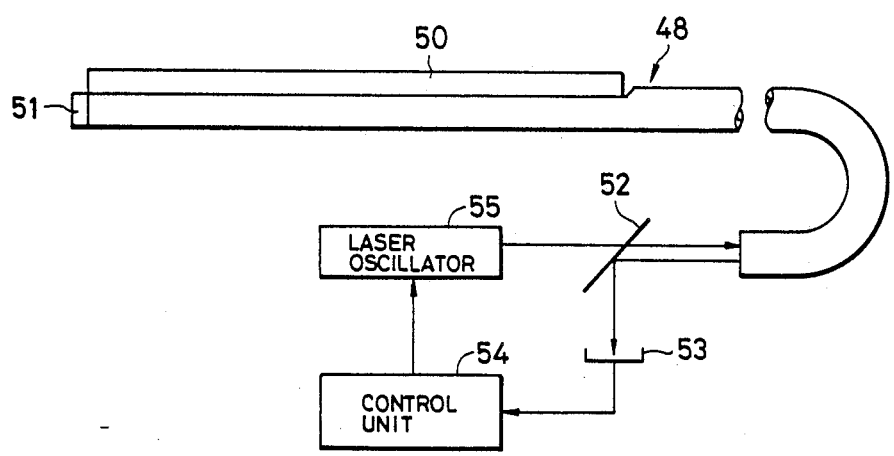

In order to promote heat balance and safety in operation by preventing overheating caused by the laser beams, and to control the bending angle of the shape-memorizing alloy with high accuracy, the foregoing mechanism for bending the elongated body preferably uses control units as depicted in FIGS. 8 and 9. In FIG. 8 there is illustrated a schematic diagram of an example of one of the control units. More specifically, the tip end surface of an optical fiber 38 is provided with a reflecting member such as a mirror or a prism, or with a reflecting part 41 coated with a reflecting film. In cooperation with a half-silvered mirror 42, a light-detecting element 43 provided at the other end of the elongated body detects the intensity of the light reflected by the reflecting part 41 which makes no contribution to the heating of a shape-memorizing alloy 40.

The outputs of a laser oscillator 45 which produces the laser beams is controlled by a control unit 44, which controls the magnitudes of the laser beams on the basis of the detected output. As a substitute for the reflecting part 41 having the above-mentioned constitution, a layer of a substance the optical characteristics of which vary according to a liquid crystal temperature may, as illustrated in FIG. 9, be formed on the tip end surface of the optical fiber 48. As in the previous case, the output of the oscillator 55 which produces the laser beams is controlled using the half-silvered mirror 52, the light-detecting element 53 and the control unit 54. In consequence, a shape-memorizing alloy 50 can be bent in a desired shape. A temperature detector for detecting the temperature of the bending region using a non-electrically powered system may be employed in order to prevent electric shock. The aforementioned control unit is thus capable of preventing overheating caused by the laser beams, enhancing the safety in operation, and accurately controlling the bending angle of the shape-memorizing alloy, even if the body temperature varies when it is employed as an endoscope.

It is satisfactory for the light serving for heating to have a wavelength which will heat the shape-memorizing alloy to a predetermined temperature. For instance, suitable light generally includes far-infrared-rays, infrared-rays and ultraviolet rays, and more preferably $CO_2$ laser beams, Ar laser beam or YAG laser beams which are coherent and have energy with a high density and a large heating efficiency.

In the above-described embodiments a fiberscope has been exemplified. However, the detection part D of the elongated body 1 is not always necessary, depending upon the object to which the device is applied to observe. Also, the application of laser beams is not confined to the heating of the shape-memorizing alloy, but can be utilized for a sensor which detects the portion to be observed.

The inventive mechanism for bending the elongated body has a simple structure and is capable of reducing the diameter of the elongated body and guide-bending the desired portions of the elongated body at a predetermined angle or to a predetermined bending degree. Hence, the bending mechanism is suitably employed especially as a catheter tip-type hemadynamometer whose tip portion is provided with a pressure sensor and an endoscope. The bending mechanism is also useful for a device for observing the interior of a machine having a complicated structure or as a manipulator thereof.

Figure 10:
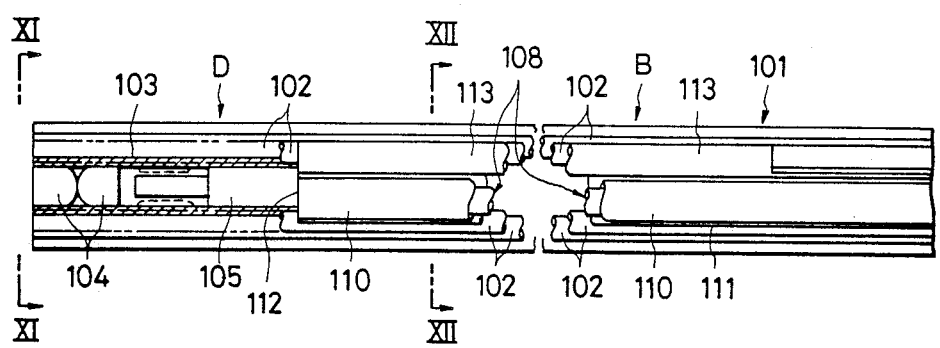
FIG. 10 is a schematic enlarged sectional view of the principal portion of a fiberscope employing a mechanism for bending an elongated body illustrating another embodiment of the present invention.
Figure 11:
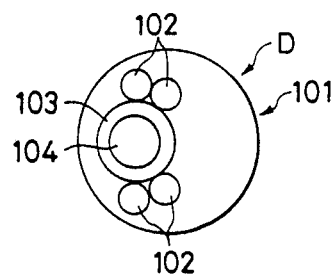
FIG. 11 is an end elevation taken substantially along a line XI—XI in FIG. 10.
Figure 12:
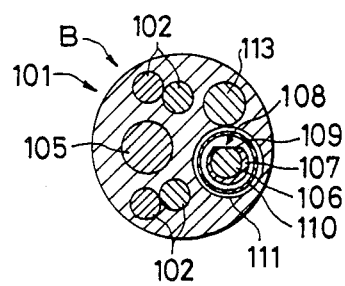
FIG. 12 is a sectional view taken substantially along a line XII—XII in FIG. 10.
Figure 13:
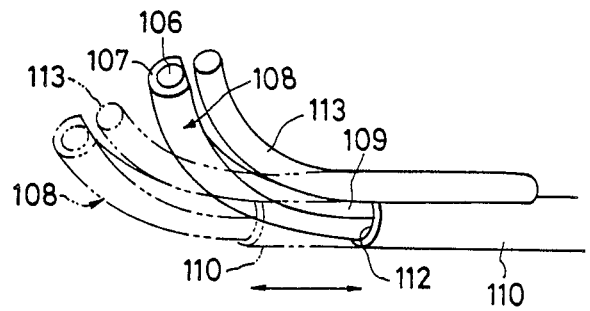
FIG. 13 is conceptual diagram of a principal portion of the elongated body showing an operational condition thereof.

Referring now to FIG. 10, there is illustrated in a schematic enlarged sectional view a principal portion of a fiberscope according to another embodiment of a mechanism for bending an elongated body. FIG. 11 is an end elevation taken substantially along a line XI—XI in FIG. 10. FIG. 12 is a sectional view taken substantially along a line XII—XII in FIG. 10. FIG. 13 is a conceptual diagram of a principal portion of the elongated body depicted in FIG. 10 illustrating an operative condition thereof.

In this embodiment, an elongated body 101 is composed of a detection part D formed at the tip of the body 101 and a bending part B incorporating a bending mechanism provided in continuation from the detection part D. Embedded in the elongated body 101 are light guides 102 for illuminating a portion to be detected, a lens sleeve 103 including object microlenses 104 disposed at the tip thereof, and a segment of image fiber 105, provided in continuation from the object microlenses 104, for leading the light emerging from the light guides 102 and reflected from the organ portion being observed. These components are combined to constitute the foregoing detection part D.

Inserted into a tube 110 capable of making a back-and-forth movement within the body 101 is an optical fiber 108 having a cladding 107 of which a predetermined portion is cut away for permitting laser beams to leak therefrom. More specifically, the tube 110 having an opening 112 formed at the tip thereof is inserted into a hollow portion 111 as to be movable longitudinally therein, this hollow portion 111 being formed in the bending part B of the body 101. The tube 110 receives the optical fiber 108 including the cladding 107 having the cut-away portion 109 cut to a predetermined length to cause the laser beams to leak from the predetermined portion.

A shape-memorizing alloy 113 assuming a linear configuration has a predetermined transformation temperature and memorizes a predetermined shape beforehand. This shape-memorizing alloy 113 is disposed in a portion adjacent the cut portion 109 of the optical fiber 108 of the elongated body 101 in order to bend the body 101 in the predetermined shape. The tip of the optical fiber 108 is fixed to the detection part D, while the shape-memorizing alloy 113 is fixed to the elongated body 101 to prevent positional deviation of the optical fiber 108 and the shape-memorizing alloy 113 caused due to the back-and-forth movement of the tube 110. The tube 110 is protrusively provided in an operating unit (not illustrated) for causing the tube 110 to advance and move backwardly so that the tube 110 alone is able to undergo this back-and-forth movement.

When moving the tube 110 forward within the hollow portion 111 formed in the body 101, the cut portion 109 of the optical fiber 108 is exposed and the shape-memorizing alloy 113 is irradiated with laser beams emerging from the cut portion 109. On the other hand, when returning the tube 110, the cut portion 109 is retracted into the tube 110, thereby shielding the laser beams. Namely, the tube 110 functions as a shutter for permitting irradiation of the laser beams on the shape-memorizing alloy and shielding the laser beams leaking from the cut-away portion 109 in association with the back-and-forth movement thereof.

The material of the various elements of the enlarged body, etc., may be the same as in the previously described embodiments.

In the above-described example, only the tube 110 is made to move. In contrast with this, it is possible for the cut-away portion 109 of the optical fiber 108 and the shape-memorizing alloy 113 to move back and forth while facing each other.

Control of the conditions under which the shape-memorizing alloy 113 is irradiated with light leaking from the cut-away portion of the optical fiber 108 may be effected in various manners depending upon the way in which the tube 110 moves. For instance, the opening may include a plurality of holes sequentially formed in the tube 110 in the longitudinal direction thereof in the case where the tube 110 is moved back and forth. In this case, when employing a shape-memorizing alloy 113 whose memorized bending rate differs gradually in the longitudinal direction, the shape-memorizing alloy 113 and the elongated body 101 can be bent in predetermined shapes sequentially at given portions according to the degree to which the tube moves back and forth.

Figure 14A:
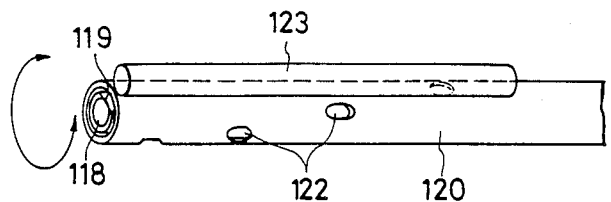
FIG. 14A is a schematic diagram illustrating another embodiment of the present invention.
Figure 14B:
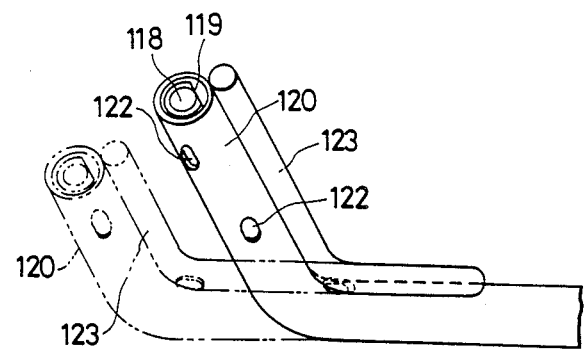
FIG. 14B is a schematic diagram illustrating a bending condition of FIG. 14A.

As illustrated in FIG. 14, a method of bending a shape-memorizing alloy 123 and the elongated body by rotating a tube 120 can be employed. More specifically, in this example a plurality of holes 122 (which substitute for the opening 112) are circumferentially formed in the tube 120 at a given spacing in the longitudinal direction thereof. The tube 120 is, as illustrated in FIG. 14A, rotated through a predetermined angle so that a desired hole 122 among the plurality of holes 122 comes to a position adjacent the cut-away portion 119 of the optical fiber 118. The laser beams leaking from the cut-away portion 119 of the optical fiber 118 are, as depicted in FIG. 14B, transmitted through the hole 122 facing the cut-away portion 119 to heat the desired portion of the shape-memorizing alloy 12, thereby bending the same. That is, the heated portion of the shape-memorizing alloy 123 can be changed by varying the rotational angle of the tube 120. Thus, it is possible to control the position at which the elongated body is bent. As in the case of the previous embodiment, when using a shape-memorizing alloy 123 whose memorized bending rate differs gradually in the longitudinal direction, the shape-memorizing alloy 123 can be bent in a desired configuration consecutively at predetermined portions in accordance with the rotational angle of the tube 120.

Figure 15A:
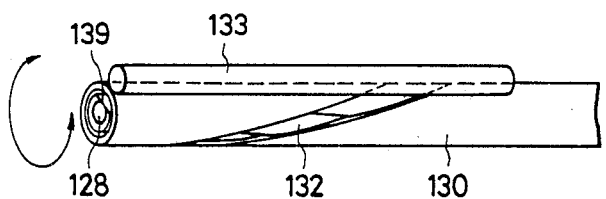
FIG. 15A is a schematic diagram of the principal portion of yet another embodiment.
Figure 15B:
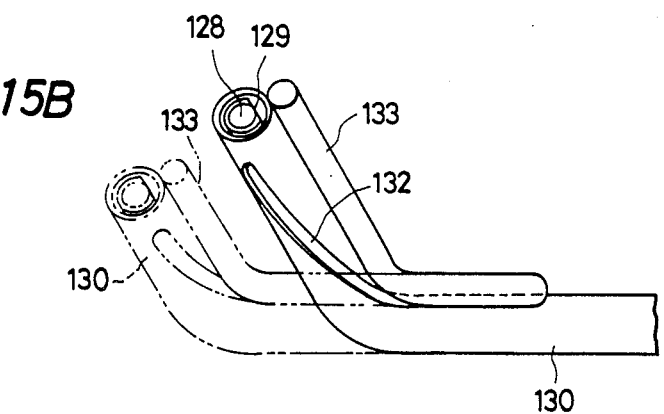
FIG. 15B is a schematic diagram illustrating a bending condition of the embodiment of FIG. 15A.
Figure 16A:
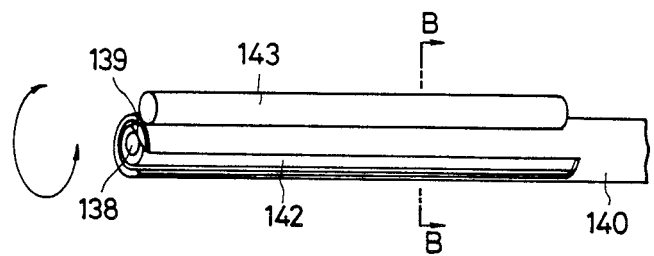
FIG. 16A is a schematic diagram of a principal portion of still another embodiment of the present invention.
Figure 16B:
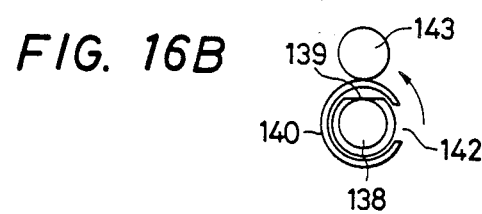
FIG. 16B is a sectional view taken substantially along a line B—B in FIG. 16A.
Figure 16C:
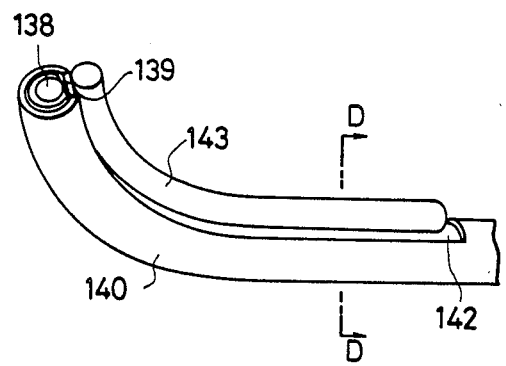
FIG. 16C is a schematic diagram showing a bending condition of FIG. 16A.
Figure 16D:
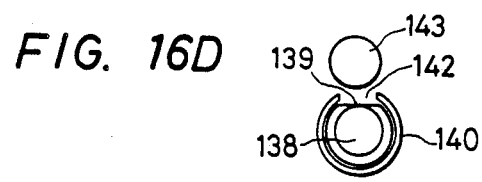
FIG. 16D is a sectional view taken substantially along a line D—D in FIG. 16C.

As shown in FIG. 15, a helical hole 132 may be formed in a tube 130 instead of holes 122 depicted in FIG. 14. In this example, a cut portion 129 of the optical fiber 128 inserted into the tube 130 and a shape-memorizing alloy 133 are, as illustrated in FIGS. 15A and 15B, disposed facing each other through the intermediary of the tube 130. With the tube 130 being formed with the helical hole 132, it is feasible to consecutively select the heated portion of the shape-memorizing alloy 133 heated with the laser beams leaking from the cut-away portion 129 of the optical fiber 128 by rotating the tube 130. The heat-bending portions of the shape-memorizing alloy 133 can thus be successively controlled simply by turning the tube 130.

Moreover, as depicted in FIG. 16, the helical hole 132 may be replaced by a linear slot 142 formed in the tube 140 in the longitudinal direction. In this example, as in the above-mentioned embodiment which employs a rotary system, the slot 142 of the tube 140 functions as a shutter. When the tube 140 rotates through a given angle, the laser beams leaking from the cut-away portion 139 of an optical fiber 138 pass through the slot 142 with the result that a shape-memorizing alloy 143 is heat-bent. In the situations depicted in FIGS. 16A and 16B, the slot 142 of the tube 140 is not positioned between the cut-away portion 139 of the optical fiber 138 and the shape-memorizing alloy 143 facing the cut-away portion 139. Consequently, the shape-memorizing alloy 143 cannot be heated with the laser beams leaking from the cut-away portion 139 of the optical fiber 138. However, the tube 140 is rotated so that the slot 142 of the tube 140 is centered between the cut-away portion 139 and the shape-memorizing alloy 140. As illustrated in FIGS. 16C and 16D, the laser beams which pass through the slot 142 of the tube 140 and leak from the cut-away portion 139 of the optical fiber 138 heat the shape-memorizing alloy 143, thereby bending it is in the predetermined shape. The amount of irradiation by the laser beams is adjusted in accordance with the rotational angle, and hence the heating temperature of the shape-memorizing alloy 143 is controlled. In addition, the restoring stress of the shape-memorizing alloy 143 can be adjusted.

In the above-described embodiment, the elongated body is bent in one direction utilizing a single segment of shape-memorizing alloy. As in the foregoing embodiments depicted in FIGS. 10 through 16, disposed within the elongated body are the optical fibers 108, 118, 128 and 138, the tubes 110, 120, 130 and 140, and the shape-memorizing alloys 113, 123, 133, and 143. The shape-memorizing alloys 113, 123, 133 and 143 are arranged to bend in different directions. In consequence, multidirectional bending of the elongated body can be performed by selecting the tubes 110, 120, 130 and 140 which are moved back and forth or rotated.

In the embodiment shown in FIGS. 10 to 13, the shape-memorizing alloy 113 is so disposed that the alloy 113 is positioned adjacent the cut-away portion 109 of the optical fiber 108 and the bending direction of the elongated body 101 is made to differ at a plurality of given portions in the longitudinal direction thereof. Depending on the longitudinal position of the tube 110, the shape-memorizing alloy 113 is irradiated with light leaking from the cut-away portions 109 of the optical fiber 108. Thus, multidirectional bending of the elongated body 101 can be effected by adjusting the position at which the shape-memorizing alloy 113 is irradiated and heated by the laser light.

In the embodiment shown in FIGS. 14 to 16, the segments of shape-memorizing alloy 123, 133 and 143 are disposed in the elongated body in such a manner that their positions differ in the peripheral direction, and hence the bending direction also differs. By adjusting the rotational angles of the tubes 120, 130 and 140, it is possible to select the shape-memorizing alloys 123, 133 and 143 which are heated by the light leaking from the cut-away portions 119, 129 and 139 of the cladding. As a result, the elongated body can be controllably bent in multiple directions.

Figure 17A:
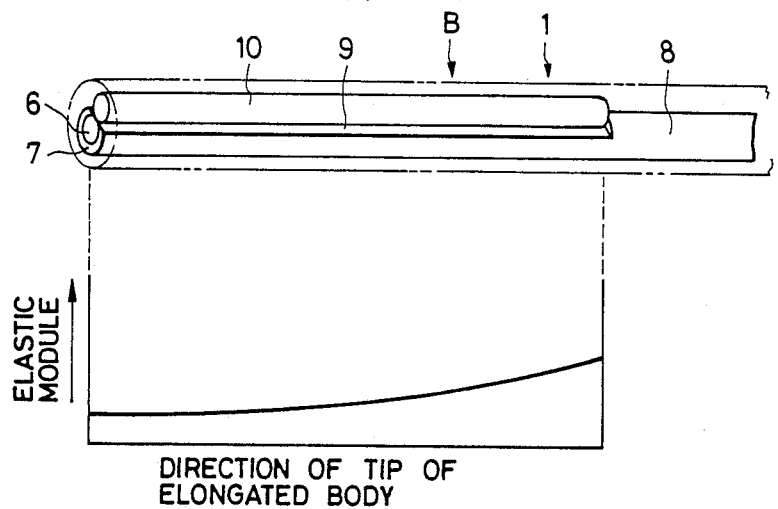
FIG. 17A is a schematic enlarged diagram showing in particular an optical fiber and a shape-memorizing alloy at a bending part (B) in FIG. 2 in accordance with a further aspect of the invention.
Figure 17B:
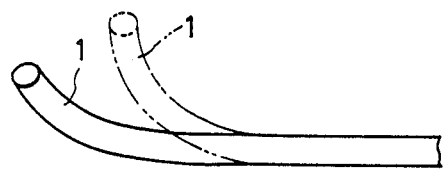
FIG. 17B is a conceptual diagram illustrating a bending condition of the elongated body of FIG. 17A.

Another embodiment of the invention will now be described with reference to FIGS. 17A and 17B. The general structure of this embodiment is the same as that shown in FIGS. 2 to 4, wherein like reference numerals indicate like elements. In this embodiment, however, the bending part B is formed by sequentially joining a plurality of synthetic resin segments each having a small elastic modulus and arranged so as to decrease the elastic modulus in the direction of the tip of the elongated body 1.

After the laser beams have travelled through the optical fiber 8, the shape-memorizing alloy 10 is heated by the laser beams leaking from the cut-away portion 9. At this time, only the tip of the elongated body 1 is, as depicted by a solid line in FIG. 17B, bent when the power of the laser beams is low because the elastic modulus of the bending part B diminishes in the direction of the tip of the body 1. If the power of the laser beams is increased, as indicated by a broken line in FIG. 17B, the body 1 as a whole is bent in a previously memorized shape. Namely, it is possible by controlling the laser beam power to bend the shape-memorizing alloy 10 and the elongated body 1 in a desired configuration in accordance with the variations in the elastic modulus of the bending part B.

The bending part B in which the shape-memorizing alloy 10 is disposed may be formed of a variety of materials. The usable materials may be classified as hard materials, such as polymethyl methacrylate and polystyrene, and soft materials, such as polyethylene, polypropylene, ethylene-vinyl acetate copolymer, acrylic resin, silicone resin, polyurethane, polyisobutylene, polybutadiene, polyisoprene and styrenebutadiene copolymer. The hard and soft materials may be joined by bonding, welding or other similar methods so that the elastic modulus of the bending part B gradually diminishes towards the tip portion.

Formation of the bending part B having an elastic modulus varying in the longitudinal direction may be done with the following methods: The thickness of the elongated body 1 at the bending part B may be gradually made smaller in the direction of the tip thereof, thus varying the thickness of the elongated body 1. A corresponding portion of the elongated body to the bending part B may be formed with a recess such as a peripheral groove. This peripheral groove is arranged so that its spacing is gradually narrowed or its width varies towards the tip of the elongated body 1. This arrangement facilitates the bending of the tip of the body 1. As in the previous case, because of the variations in thickness or the formation of the recess such as a peripheral groove, the shape-memorizing alloy 10 and the elongated body 1 can be bent in desired shapes in accordance with the variations in the elastic modulus of the bending part B.

Figure 18:
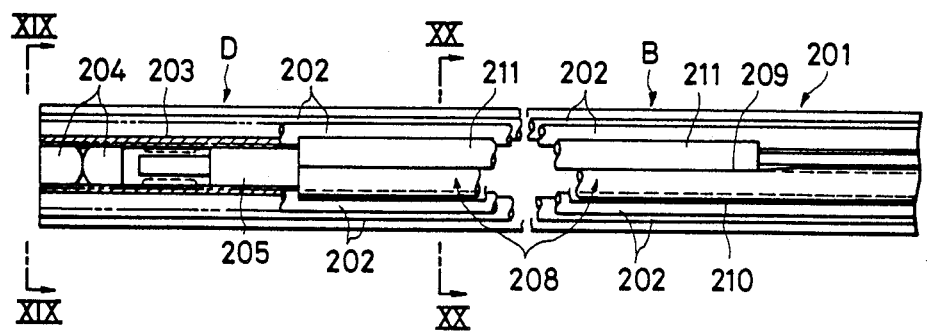
FIG. 18 is a schematic enlarged sectional view of the principal portion of a fiberscope utilizing a mechanism for bending an elongated body illustrating a still further embodiment of the present invention.

Referring now attention to FIG. 18, there is illustrated a schematic enlarged sectional view of a principal portion of a fiberscope employing a further embodiment of a mechanism for bending an elongated body.

Figure 19:
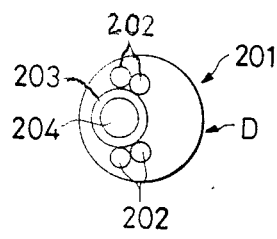
FIG. 19 is an end elevation taken substantially along a line XIX—XIX in FIG. 18.
Figure 20:
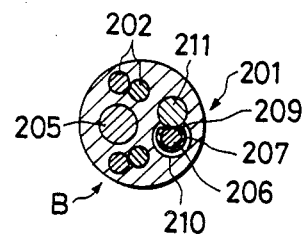
FIG. 20 is a sectional view taken substantially along a line XX—XX in FIG. 18.
Figure 21:
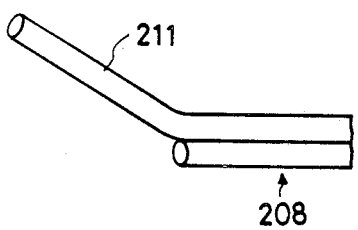
FIG. 21 is a conceptual diagram of the principal portion of the elongated body depicted in FIG. 18. showing an operational condition thereof.

FIG. 19 is an end elevation taken substantially along a line XIX—XIX in FIG. 18. FIG. 20 is a sectional view taken substantially along a line XX—XX in FIG. 18. FIG. 21 is a conceptual diagram of a principal portion, illustrating an operational condition of the elongated body shown in FIG. 18.

An elongated body 201 is constituted by a detection part D formed at the tip of the body 201 and a bending part B including a bending mechanism provided in continuation from the detection part D. Embedded in the elongated body 201 are light guides 202 for illuminating a portion to be observed, a lens sleeve 203 including objective microlenses 204 disposed at the tip thereof, and a segment of image fiber 205, provided in continuation from the object microlenses 204, for leading the light emerging from the light guides 202 and reflected from the portion being observed. These components are combined to constitute the foregoing detection part D. The bending part B disposed adjacent to the embedded components of the detection part D is composed of an optical fiber, generally indicated at 208, thus includes a core 206 for leading laser beams employed for heating purposes and a cladding 207 having a refractive index smaller than that of the core 206. This much of the structure is generally the same as that illustrated in FIGS. 2 to 4.

In accordance with this embodiment, the optical fiber 208 is inserted into a hollow portion 210, dedicated for use by this one optical fiber, which is formed in the elongated body 201 in such a manner that the optical fiber 208 is capable of undergoing a back-and-forth movement therein. As in the first-described embodiment, a predetermined portion of the cladding 107 is cut away to a given length, thus forming a cut-away portion 209. This cut-away 209 serves to permit leakage of the laser beams from the predetermined portion.

When the laser beams travel through the optical fiber 208, the temperature at the tip of the optical fiber 208, i.e., in this example, the temperature in the vicinity of the cut-away portion 209, remarkably increases. The laser beams which leak from the cut-away portion 209 heat, as illustrated in FIG. 21, the shape-memorizing alloy 211, thus bending the alloy 211 in a predetermined shape.

When the optical fiber 208 is moved back and forth within the hollow portion 210, the heat can be applied to a desired portion of the shape-memorizing alloy 211 by use of the heated tip of the optical fiber 208 in accordance with the degree to which the optical fiber 208 is moved in the longitudinal direction. Moreover, the shape-memorizing alloy 211 can be heated with the laser beams leaking from the cut portion 209 of the optical fiber 208. That is, the light leaking from the cut-away portion 209 and the heated tip of the optical fiber cooperate to efficiently heat the shape-memorizing alloy 211, resulting in the bending of the alloy 211 in the predetermined configuration.

In the thus-constructed bending mechanism, the cladding 207 at the tip of the optical fiber 208, which reaches the highest temperature, is cut away, and the shape-memorizing alloy 211 is disposed at a position corresponding to the cut-away portion 209 within the body 201. The optical fiber 208 admits the laser beams and is adjusted in position longitudinally, whereby a designated portion of the shape-memorizing alloy 211 can be heated with the laser beams leaking from the cut-away portion 209 in cooperation with the tip of the optical fiber 208 which reaches a high temperature. Hence, no troublesome wire-manipulating operation is required as in the conventional mechanism. The shape-memorizing alloy 212 and the elongated body 201 can be bent in the predetermined shapes by adjusting the amount of longitudinal movement of the optical fiber 208.

The temperature of the tip of the optical fiber 208 remarkably increases simply by leading the laser beams through the optical fiber 208, and hence the cut-away portion 209 is not always necessary. The shape-memorizing alloy 211 may be heated only by the heated tip of the optical fiber. In the case though where the cut-away portion 209 is formed in the cladding 207, the cut-away portion 209 should be provided at a position within the movable range of the optical fiber 208, corresponding to the position where the shape-memorizing alloy 211 is disposed.

Figure 22:
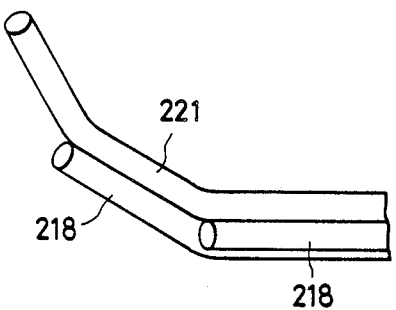
FIGS. 22 and 23 are schematic diagrams each showing principal portions of other embodiments of the present inventions.
Figure 23:
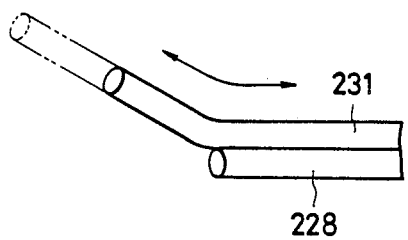

As illustrated in FIG. 22, a shape-memorizing alloy 221 is heat-bent at a plurality of portions by the heated tip of the optical fiber 218. For this purpose, the optical fibers 218 may be longitudinally movably provided in positions of a plurality of optical fiber hollow portions (not illustrated) corresponding to the shape-memorizing alloy 221, the hollow portions being formed with varying lengths. In this example, selection of the heated portions of the shape-memorizing alloy 221 can be effected by properly selecting the optical fibers 218 for leading the laser beams among the plurality of optical fibers 218. Thus, the shape-memorizing alloy 221 and the elongated body can be bent at desired portions.

The above-described embodiment shown in FIG. 22 employs a shape-memorizing alloy 221 of a type in which different configurations are memorized in a plurality of position corresponding to the bottoms of the respective optical fiber hollow portions. The laser beams are simultaneously or separately applied through the plurality of optical fibers, and thus the shape-memorizing alloy 221 can thereby be bent at a plurality of desginted portions.

In the foregoing example, the bending portions of the shape-memorizing alloys 211 and 221 are controlled by moving the optical fibers 208 and 218 longitudinally movably provided in a hollow portion (not illustrated) corresponding to the shape-memorizing alloy, or alternatively there is provided a shape-memorizing alloy whose transformation temperature and memorized configuration differ in a plurality of positions. These arrangements also yield the same effects as those in the aforementioned examples.

Figure 24:
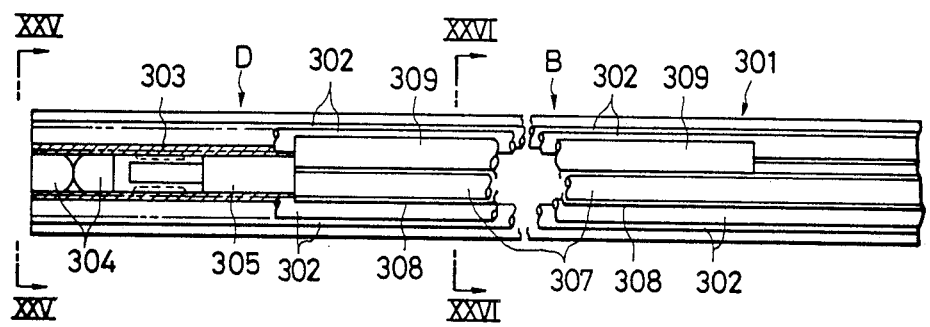
FIG. 24 is an enlarged schematic sectional view of a principal portion of a mechanism for bending an elongated body of a further embodiment used in a fiberscope.
Figure 25:
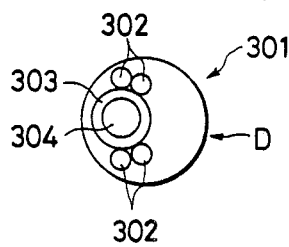
FIG. 25 is an end elevation taken substantially along a line XXV—XXV in FIG. 24.
Figure 26:
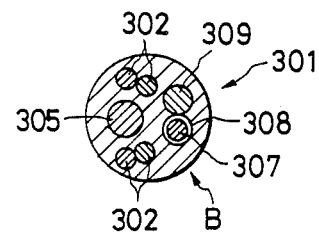
FIG. 26 is a sectional view taken substantially along a line XXVI—XXVI in FIG. 24.
Figure 27:
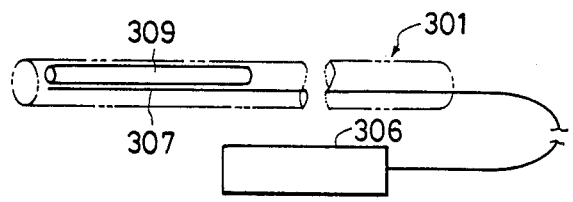
FIG. 27 is a schematic diagram illustrating a mechanism for bending the elongated body of FIG. 24.

Referring now to FIG. 24, there is illustrated a schematic enlarged sectional view of a principal portion of a fiberscope which employs a mechanism for bending an elongated body constructed in accordance with a still further embodiment of the present invention. FIG. 25 is an end elevation taken substantially along as line XXV—XXV in FIG. 24. FIG. 26 is a sectional view taken substantially along a line XXVI—XXVI in FIG. 24. FIG. 27 is a conceptual diagram of a principal portion, illustrating an operational condition of the elongated body shown in FIG. 24.

An elongated body 301 is constituted by a detection part D formed at the tip of the elongated body 301 and a bending part B including a bending mechanism provided in continuation from the detection part D. Embedded in the elongated body 301 are light guides 302 for illuminating a portion to be observed, a lens sleeve 303 including objective microlenses 304 disposed at the tip thereof, and a segment of image fiber 305, provided in continuation from the objective microlenses 304, for leading the light emerging from the light guides 302 and reflected from the portion to be observed. These components are combined to constitute the foregoing detection part D. This much of the structure is generally the same as that illustrated in FIGS. 2 to 4.

In accordance with this embodiment of the invention, a linear vibrating member 307 connected to an exciter 306 is disposed in sliding contact with a predetermined portion within the elongated body 301. More specifically, the elongated body 301 is formed with a hollow portion 308 leading to the bending part B. The vibrating member 307 is inserted into this hollow portion 308. The vibrating member 307 is slidably contactually disposed in a portion within the hollow portion 308 corresponding to the bending part B. Upon excitation of the exciter 306, the vibrating member 307 vibrates to produce friction with a wall of the hollow portion 308 which corresponds to the bending part B, with the result that the bending part B emits heat because of the thus-produced frictional heat. In this example, the inner wall of the hollow portion 308 excluding the bending part B is smoothly formed of a material having a small frictional resistance to minimize the emission of heat in the portions other than the bending part B.

In order to bend the elongated body 301 in a predetermined shape with the aid of the frictional heat, a shape-memorizing alloy 309 having a linear configuration and having a preset transformation temperature is disposed in such a portion within the elongated body 301 as to correspond to the bending part B with which the vibrating member 307 is in sliding contact.

For the purpose of enhancing the amount of heat emission due to the friction between the vibrating member 307 and the inner wall of the hollow portion 308 in the bending part B, it is preferable that inner surface of the hollow portion 308 be roughly formed, or a frictional member provided in the hollow portion 308.

The elongated body 301 excluding the bending part B, or least the inner wall of the hollow portion 308, is formed of a material having a small frictional resistance. Suitable materials include fluorine-series polymers such as polytetrafluoroethylene and polyhexafluoroproplylene, and silicone resin. Alternatively, the inner surface of the hollow portion 308 can be coated with a fluorine-series oil or silicone series oil, which contributes to a reduction in frictional resistance.

The vibrating member 307 may be constructed of linear members formed from various materials, for example, metal. The portion of the vibrating member 307 which corresponds to the bending part B is preferably formed with minute roughness.

The bending mechanism having the above-described construction is arranged such that the vibrating member 307 connected to the exciter 306 is slidably contactually disposed in the hollow portion 308 at a position corresponding to the bending par B of the elongated body 301, and the shape-memorizing alloy 309 is provided within the bending part B of the elongated body 301. In this arrangement, when the vibrating member 307 is excited by the exciter 306, the vibrating member 307 vibrates in the hollow portion 308, resulting in the generation of friction with the wall of the hollow portion 308. This friction produces heat with which the shape-memorizing alloy 309 is heated.

Therefore, unlike the conventional bending mechanism, there is no necessity to provide the multiplicity of nodal rings and the wires employed for the bending operation, resulting in a simplified structure and in a reduction in the diameter of the elongated body. As in the previously described embodiments, it is possible to attain for the elongated body an extremely small outside diameter of 2.0 mm or less.

Because the shape-memorizing alloy 309 is heated with frictional heat, no danger of causing an electric shock is presented. Hence, an endoscope employing the invention is very safe.

The bending part B may be formed at any desired position along the elongated body 301. It is, however, preferable that the bending part B be provided at the tip of the elongated body 301 to facilitate the observation of the desired organ portion.

In the hollow portion at the bending part B, the spacing between the vibrating member 307 and the hollow portion 308 can be variously set depending on the relationship between the excitation intensity of the exciter 306 and the desired heating temperature. In the above-described embodiment, the heating temperature increases in the bending part B. However, heat may be generated throughout the entire hollow portion 308 of the elongated body 301 by forming a partially hollow portion corresponding to the bending part B and the remainder in the same way without roughening the inner surface of the hollow portion 308 corresponding to the bending part B. In this case, the transformation temperature of the shape-memorizing alloy 309 is set to an allowable value depending upon the application. For instance, where the invention is applied to an endoscope, as in the previous case, the transformation temperature is set to a value slightly higher than in vivo the temperature. As a result, the elongated body 301 can be bent by the bending part B incorporating the shape-memorizing alloy 309 in such a state that the heating temperature in the hollow portion excluding the bending part B is kept low.

The shape-memorizing alloy 309 may be exposed to the hollow portion 308 so as to face to the vibrating member 307.

The shape-memorizing alloy 309 may previously memorize a configuration having the same or different bending angle or bending degree with respect to a plurality of respective portions in the longitudinal direction. Where a plurality of shape-memorizing alloys which have different transformation angles and memorize the same or different configurations beforehand are provided within the bending part B of the elongated body 301, the heating temperature can be adjusted by varying the exciting intensity of the exciter 306. Hence, the bending portions and the bending configurations of the shape-memorizing alloys can easily be selected.

In the above-described embodiment, the elongated body 301 is arranged to be bent in one direction utilizing a single segment of shape-memorizing alloy 309. However, a plurality of vibrating members 307 and a several of shape-memorizing alloys 309 can be provided in the elongated body 301 in the same manner as that described above in order to mutidirectionally bend the elongated body 301. More specifically, for example, when employing four segments of vibrating member 307 and also four segment of shape-memorizing alloy 309, the vibrating member 207 can be disposed within the elongated body 301 in a state where one pair of vibrating members 307 facing each other are arranged orthogonally to another pair of vibrating members 307. The shape-memorizing alloys 309 are provided in the slide-contacting portions of the individual vibrating members 307. By selectively exciting the four segments of vibrating member 307, the elongated body 301 can be selectively bent in four directions.

The primary requirement for the exciter 306 of course to cause the vibrating member 307 to vibrate. For this purpose, the exciter 306 may be implemented with an ultrasonic exciter to efficiently excite the vibrating member 307 and to facilitate the control of the heating temperature of the bending part (B). The exciting element of the ultrasonic exciter may be formed by various well-known conventional elements such as a piezoelectric crystal vibrator, an electrostrictive vibrator made of $BaTiO_3$, a magnetostrictive vibrator, etc.

The mechanism for bending the elongated body has a simple structure and is capable of attaining a reduced diameter of the elongated body and guide-bending the desired portions of the elongated body at a predetermined angle or to a predetermined bending degree.

As discussed above, the mechanism for bending the elongated body according to the present invention provides the following effects: Since the shape-memorizing alloy is set in the cut-away portion of the cladding of the optical fiber, when the light serving for heating travels through the optical fiber, portions of the light leaks from the cut-away portion. Subsequently, the shape-memorizing alloy is heated, thereby bending the alloy i the previously memorized configuration. The elastic modulus of the optical fiber is selected such that, when the shape-memorizing alloy cools, the already-bent shape-memorizing alloy and elongated body are restored to their initial shapes by the elastic restoring force of the optical fiber. It is therefore feasible to reversibly bend and restore the elongated body in desired patterns by a simple operation with high accuracy. Because no nodal ring and wire are required, the structure can be simplified, and the diameter of the elongated body reduced. In addition, since heating the shape-memorizing alloy involves only the use of light, there is no possibility of causing electric shock, thus leading to safety in operation.

As further discussed above, in the mechanism for bending an elongated body according to a further embodiment of the present invention, a vibrating member is slidably contactually provided in a predetermined portion within the elongated body. Therefore, when the vibrating member is vibrated by the exciter, the temperature of the slide-contacting portion can be increased due to frictional heating. The heating temperature due to such frictional heating can be controlled by adjusting the exciting intensity of the exciter. The shape-memorizing alloy is disposed in a portion within the elongated body corresponding to the slide-contacting portion of the vibrating member. Consequently, the shape-memorizing alloy is heated with frictional heat, and the alloy can thereby be bent in the previously memorized shape.

The elastic modulus of the elongated body and the optical fiber is thus controllably adjusted, and when the shape-memorizing alloy cools, the already-bent shape-memorizing alloy and elongated body can be restored to their initial shapes by the elastic restoring force of the elongated body and the optical fiber. It is therefore possible to reversibly bend and restore the elongated body in predetermined shapes by a simple operation with high accuracy. Because no nodal ring and wire are required, the overall structure is simplified, and the diameter of the elongated body can be reduced. In addition, because the heating of the shape-memorizing alloy involves only the use of light or frictional heat there is no danger of electric shock, providing a very safe operation.

What is claimed is:

1. In a mechanism for bending an elongated body including an optical fiber, the improvement wherein said optical fiber comprises a core for leading a heating light beam and a cladding and a shape-memorizing alloy is disposed in a portion within said elongated body corresponding to a tip of said optical fiber such that said shape-memorizing alloy is heated by said tip of said optical fiber thereby bending said shape-memorizing alloy and in turn said elongated body and said optical fiber.

2. In a mechanism for bending an elongated body including an optical fiber, the improvement wherein said optical fiber comprises a core for leading a heating light beam and a cladding and a shape-memorizing alloy is disposed in a portion within said elongated body corresponding to a tip of said optical fiber such that said shape-memorizing alloy is heated by said tip of said optical fiber thereby bending said shape-memorizing alloy and in turn said elongated body and said optical fiber, wherein at least one of said optical fiber and said shape-memorizing alloy is mounted in said elongated body in such a manner as to be movable longitudinally therein.

3. The mechanism for bending an elongated body as set forth in claim 2, wherein said optical fiber is longitudinally movably mounted in said elongated body.

4. The mechanism for bending an elongated body as set forth in claim 2, wherein a plurality of optical fibers are longitudinally movably mounted in said elongated body, the positions of said elongated body.

5. The mechanism for bending an elongated body as set forth in claim 2, wherein said shape-memorizing alloy is longitudinally movably mounted in said elongated body.

6. The mechanism for bending an elongated body as set forth in claim 2, wherein said elongated body comprises a portion of an endoscope including an image fiber.

7. In a mechanism for bending an elongated body including an optical fiber, the improvement wherein said optical fiber comprises a core for leading a heating light beam and a cladding and a shape-memorizing alloy is disposed in a portion within said elongated body corresponding to a tip of said optical fiber such that said shape-memorizing alloy is heated by said tip of said optical fiber thereby bending said shape-memorizing alloy and in turn said elongated body and said optical fiber, wherein a predetermined portion of said cladding at said tip of said optical fiber is cut away.

8. The mechanism for bending an elongated body as set forth in claim 7, wherein said optical fiber is longitudinally movable mounted in said elongated body.

9. The mechanism for bending an elongated body as set forth in claim 7, wherein said elongated body comprises a portion of an endoscope including an image fiber.

* * * * *